United States Patent [19]

Johnson et al.

[11] 4,263,103

[45] Apr. 21, 1981

[54] PROCESS FOR THERMALLY STABILIZING STEROLS BY DEGASSING AND FLASH DISTILLING

[75] Inventors: Ralph F. Johnson, Crystal; Jimmy A. De Mars, Blaine, both of Minn.

[73] Assignee: Henkel Corporation, Minneapolis, Minn.

[21] Appl. No.: 101,410

[22] Filed: Dec. 10, 1979

Related U.S. Application Data

[62] Division of Ser. No. 810,552, Jun. 24, 1977, Pat. No. 4,198,276.

[51] Int. Cl.³ ............................ B01D 3/06; C07J 9/00
[52] U.S. Cl. ...................................... 203/88; 203/6; 203/39; 203/91; 260/397.25
[58] Field of Search .................. 203/6, 88, 39, 91, 89; 260/397.25

[56] References Cited

U.S. PATENT DOCUMENTS

| | | | |
|---|---|---|---|
| 2,054,096 | 9/1936 | Potts et al. | 203/88 |
| 2,146,894 | 2/1939 | Hickman | 260/397.25 |
| 2,180,356 | 11/1939 | Hickman | 203/88 |
| 2,527,602 | 10/1950 | Wall | 260/397.25 |
| 2,674,570 | 4/1954 | Potts | 203/88 |
| 2,755,235 | 7/1956 | Governale | 203/6 |
| 2,866,739 | 12/1958 | Ciesielski et al. | 260/397.25 |
| 3,879,431 | 4/1975 | Clark et al. | 260/397.25 |
| 3,887,537 | 6/1975 | Harada et al. | 260/397.25 |

*Primary Examiner*—Wilbur L. Bascomb, Jr.
*Attorney, Agent, or Firm*—Forrest L. Collins; Patrick J. Span

[57] ABSTRACT

This invention describes a method for thermally stabilizing sterols to permit economic recovery of the sterols present in a sterol containing source material.

9 Claims, No Drawings

PROCESS FOR THERMALLY STABILIZING STEROLS BY DEGASSING AND FLASH DISTILLING

This is a division of application Ser. No. 810,552, filed June 24, 1977, now U.S. Pat. No. 4,198,276.

BACKGROUND OF THE INVENTION

This invention relates to the processing and recovery of sterols.

DESCRIPTION OF THE ART

Sterols are polycyclic alcohols derived from plant or animal sources. The sterols are useful in varied applications such as preparing steroid intermediates for hormones, and as well for use as emulsifiers.

In, for example, the field of steroid chemistry various sterols are modified by oxidation, acylation, esterification or de-esterification to form synthetic hormones. The purity of the sterol used to form the steroid hormones must be quite high to ensure that the desired end product is obtained of sufficient quality and quantity. The difficulty in obtaining steroids from the corresponding sterols is complicated by the fact that the individual sterols are usually found in mixture with other sterols. The separation of one sterol from another in a mixture is extremely difficult. The difficulty arises from the fact that most sterols differ from one another only in the side chain and then only by the presence of one or two additional carbon atoms. Even more difficult, is the separation of sterols which differ only in the degree of saturation of the side chain, and even more difficult is the separation of the optical isomers of the various sterols.

It was previously discussed in U.S. Pat. No. 3,879,431 issued to Clark, DeMars, and Wilson on Apr. 22, 1975 that sterols could be purified by distillation. This patent, which is herein incorporated by reference, discloses a method for separating campesterol and sitosterol from a mixture containing both the sterols. Sitosterol and campesterol differ only in that the former compound contains an ethyl group pendent from the 24 carbon position whereas the latter compound is substituted with a methyl radical in the same position. Thus, as is stated in the Clark et al. patent, sitosterol and campesterol were believed difficult, if not impossible, to commercially separate in their respective free forms.

The method described in the Clark et al patent for the separation of sitosterol and campesterol is briefly described as follows. Vegetable oils, such as soy bean oil, cottonseed oil, safflower oil, peanut oil, rice oil, and other similar oils contain sitosterol, campesterol and other sterols such as stigmasterol at a level of generally less than 0.5% by weight. Another suitable source which contains these sterols is tall oil. These oils, are treated by saponification, extraction, and crystallization followed by distillation and high pressure propane extraction to concentrate the sterols while removing other valuable by-products present in the oils.

The concentrated sterol mixture is often the by-product of commercial processes for obtaining soap or during the vegetable oil deodorization process. In the first instance, soap is extracted by saponifying the sterol esters to yield the soap and the free sterol. In the vegetable oil deodorization step the concentrated sterol mixture (sludge) is obtained following steam sparging which is done to eliminate the unpleasant odors present in, for instance, crude soy bean oil.

The free sterols obtained from soap processing or oil deodorization are then separated from other components present in the sterol mixture by solvent extraction. Alternatively, the unsaponifiable components may be removed from a mixture of the free sterols and soap as described in U.S. Pat. No. 2,843,610 issued to Brown et al. on July 15, 1958.

In any event, it suffices to say that concentrated sterol mixtures may be obtained approximating 90% pure free sterols. The impurities left with the sterols include alcohols, solvents such as ethylene dichloride or methanol, water and inorganic salts such as sodium chloride or sodium sulfate which were carried through from earlier processing. It is stated in Clark et al. that the alcohols, ethylene dichloride, and water may be removed by distillation leaving the sterols in the residue with the inorganic salts.

The residue is then distilled to provide a fraction or fractions enriched in campesterol leaving a residue fraction enriched in sitosterol due to the differential boiling points of the sterols. The distillation for these sterols is generally carried out between 0.05 and 3.5 millimeters of Hg and a vapor temperature of between 225° C. and 270° C. It is further stated that fractionation according to Clark et al. is carried out in which the residence time of the sterols in the still has been up to 15 minutes and in some instances even longer residence times.

It is now been found, that in processing sterols such as those described in Clark et al. and in general any sterol including zoosterols that serious degradation can take place during the distillation process. The type of degradation referred to has been identified as dehydration of the hydroxyl functionality in the A ring. It is also believed, that some dehydration-condensation may occur in the distillation process. It has further been found that the sterol degradation, of whatever form, is related to the residence time and temperature which the sterol reaches in the distillation process. In fact, the amount of degradation which occurs during the distillation may exceed the rate of purification.

It has now been found that trace amounts of a Friedel-Crafts catalyst present in the sterol mixture is responsible for forming the dehydrated sterol materials. The present invention is directed to a method for avoiding the degradation of sterols during the purification or separation described in Clark et al.

Throughout the specification and claims percentages and ratios are by weight, temperatures are in degrees Celsius, and absolute pressures are indicated as millimeters of mercury unless otherwise indicated.

SUMMARY OF THE INVENTION

The present invention describes the process of thermally stabilizing sterols in a sterol containing source material which has present therein a Friedel-Crafts catalyst. The sterol containing source material is first rapidly distilled to yield a distillate containing the sterols which are substantially free of the Friedel-Crafts catalyst. The sterols are present in the distillate in about the same relative proportions as in the sterol containing source material prior to distillation.

The present invention also describes the process of purifying sterols from a sterol containing source material having present therein sterols and ferric chloride wherein the sterol containing source material is first degassed and then subjected to flash distillation to yield as a distillate the sterols wherein the sterols are in about the same relative proportion to one another as in the sterol containing source material, and a residue containing the ferric chloride.

DETAILED DESCRIPTION OF THE INVENTION

The present invention, as stated above, is concerned with the purification and separation of sterols without the resultant loss of the sterols due to the formation of a dehydrated by-product. The thermal stability of the sterols has been found to be dependent upon the presence of Friedel-Crafts catalysts in the sterol containing source material. Typical examples of Friedel-Crafts catalysts include sulfuric acid, boron trifluoride, hydrochloric acid, aluminium chloride, aluminium bromide and ferric chloride. As a practical matter, ferric chloride and aluminium chloride, most particularily ferric chloride are the most troublesome Friedel-Crafts catalysts. None of the foregoing Friedel-Crafts catalysts should of course be included in a sterol containing source material which is to be processed according to the Clark et al patent due to the high potential for degradation of the sterols. However, from a practical standpoint, the true metallic compounds such as aluminium chloride or ferric chloride have a reasonable probability of occurring in the sterol containing source materials due to processing conditions.

Specifically, ferric chloride may be present in the sterol containing source material from several sources. First, most of the sterols with which the present invention is concerned are obtained from plant sources and thus iron may be carried into the sterol containing source material from, for instance, the soy beans or soil which adheres to the soy beans. The chloride anion may be present in the sterol containing source material by the use of the hydrochloric acid during processing steps such as the acidification of soaps to form free fatty acids. During processing the iron source and chloride source may react to form ferric chloride thus accounting for the presence of a Friedel-Craft catalyst in the sterol containing source material. It is also likely that water containing high hardness levels also supplies ferric chloride to the sterol containing source material during processing. Another potential source of ferric chloride or for that matter aluminium chloride in the sterol containing source material is from leaching of those components from the vessel in which the source material is being processed.

It has been established that as few as 100 parts per million of a Friedel-Crafts catalyst in the sterol containing source material will have a significant effect on the yield and purity of the sterols processed under the conditions of the Clark et al patent. Due to the inherent nature of catalytic activity it must be appreciated that even minute amounts of the Friedel-Crafts catalyst present in the sterol containing source material will affect the purity and yield of the sterols.

The sterol containing source material is conveniently any form of concentrated sterols for which purification is required. While the present invention is mainly concerned with thermally stabelizing soy sterols which are predominately a mixture of sitosterol, campesterol, and stigmasterol, any other source of sterols will be benefited by the thermal stabilization of the present invention. Other such sterol containing source materials include tall oil sterols, wheat germ oil sterols, and as well zoosterols including cholesterol. It is to be understood, that it is not necessary that the sterol containing source material be a mixture of sterols as a single sterol material which has been contaminated with a Friedel-Crafts catalyst will be benefited by processing according to the present invention. In the case of using a single sterol, it is noted that there is no requirement for the proportion of the sterols to be substantially the same as in the source material.

The distillation apparatus employed to separate the sterols from the Friedel-Crafts catalyst is a wiped film evaporator. The basic construction of a wiped film evaporator is a circular sealed vessel upon which an appropriate vacuum source is attached. The sterol containing source material is fed as a liquid into the top of the wiped film evaporator and allowed to flow down the walls of the evaporator as a thin film. The thinness of the film is controlled by a series of blades extending radially from a shaft extending upward through the center of the wiped film evaporator. The rotating blades spread the film evenly and thinly throughout the walls of the wiped film evaporator. The walls themselves are heated to an appropriate temperature to vaporize the sterols in the sterol containing source material. The vapors containing the sterols condense on the surface of a conduit (heat exchanger) located below the shaft concentric thereto. The conduit is itself heated above the melting point of the lowest melting component of the sterol containing source material to ensure that the condensate does not solidify upon the shaft. Below the shaft is a sump which is used to collect the sterols which condense and flow down the shaft. At the bottom of the outer walls of the wiped film evaporator a reservoir is established. This reservoir collects that portion of the sterol containing source material containing the Friedel-Crafts catalyst and that portion of the higher boiling organic components in the sterol containing source material which have not been evaporated. Both the reservoir containing the residue and the sump containing the sterols free of the Friedel-Crafts catalyst are constructed so that the residue and the sterols may be drawn off to allow continuous processing.

It should also be noted that the blades which scrape the outer wall of the wiped film evaporator are rotated at sufficiently high speed to ensure that any material condensing on the blade is thrown back onto the outer walls. This centripetal action of the blades provides two important advantages. First, it ensures that the blade structure of the wiped film evaporator is self-cleaning. Secondly, in operating the wiped film evaporator it is invariable that some spattering will occur from the outer walls onto the blades. The spattered material may contain small amounts of the Friedel-Crafts catalyst. Thus, the centripetal action significantly reduces the possibility that any of the Friedel-Crafts catalyst will be carried to the conduit and thus contaminate the purified sterol collected in the sump. It is noted, that it is possible to conduct consecutive purification steps with one or more wiped film evaporators if a significant portion of Friedel-Crafts catalyst is present in the sterols collected in the sump.

Suitable wiped film evaporators include Pfaudler Sybron Corporations Manufacture Number 55545 and Model Number 4.2-12C-WFE-19. While the wiped film evaporator is the recommended apparatus for the present invention, any other suitable apparatus which functions similarily to eliminate the Friedel-Crafts catalyst from the sterols may be utilized. Such apparatus include falling film and thin film evaporators.

In conducting the distillation according to the present invention the residence time of the sterol containing source material in the distillation apparatus should be held to less than 15 minutes to avoid substantial degradation of the sterols. It is recognized that operating under the conditions of distillation periods of 10 minutes or less, preferably less than 5 minutes, more preferably less than 1 minute and most preferably less than 30 seconds residence time are desirable.

The vacuum imposed upon the sterol containing source material in the distillation apparatus is conveniently maintained at from about 0.01 to about 10 millimeters, more preferably 0.05 to about 7 millimeters, and most preferably from about 0.1 to about 4 millimeters Hg absolute.

The distillation temperature is conveniently set such that the sterols are rapidly driven off during the distillation operation. This temperature depending upon the pressure in the distillation apparatus will generally be in the region of about 160° C. to about 265° C., preferably from about 190° C. to about 250° C. The vapor temperature will be measured, as in a wiped film evaporator, at a point midway between the heated walls and the conduit upon which the condensation of the sterols takes place.

It will be recognized at this point that the actual temperature of the walls of the distillation apparatus and the sterol containing source material will be in excess of the vapor temperature of the distillate. Thus, to avoid substantial decomposition of the sterols by the Friedel-Crafts catalyst on the walls of the distillation apparatus the operation is preferably conducted such that less than 15% by weight of the sterol containing source material reaches a temperature of greater than 300° C., preferably less than 260° C. The residue containing the Friedel-Crafts catalyst collected in the reservoir at the bottom of the distillation apparatus is not considered to be a portion of the sterol containing source material for the aforementioned temperature requirement.

The amount of residue which is collected in the reservoir at the bottom of the distillation apparatus is typically less than about 30% by weight, preferably less than about 10% by weight of the sterol containing source material fed into the distillation apparatus.

It is observed, that it is desirable that the sterol containing source material is not subjected to temperatures which cause decomposition of the sterols prior to conducting the thermal stabilizing distillation of the present invention. In accordance with the foregoing statement, the temperature of the sterol containing source material in a holding vessel prior to conducting the thermal stabilization of the present invention should be maintained in the range of from about 135° C. to about 200° C., preferably from about 140° C. to about 170° C. The lower temperature of the foregoing range is effectively set to maintain the sterols in the sterol containing source material in a liquid state while the upper limits are set by the point at which loss of the sterol due to decomposition is unacceptable.

It is noted that by conducting the process of the present invention that the efficiency of the operation in the Clark et al patent can be substantially improved. By efficiency it is meant that both the purity and the yield of the sterols distilled is vastly improved.

The following are examples of the present invention:

EXAMPLE I

A phytosterol containing source material having present therein 50 parts sitosterol, 25 parts campesterol, 5 parts stigmasterol, 20 parts of various organic impurities and 100 parts per million ferric chloride is obtained from soy bean oil residue. This sterol containing source material is heated to a temperature of about 140° C. to ensure that all of the components are fluid.

The sterol containing source material is fed into a wiped film evaporator which is 0.4 meter high and 0.3 meter in diameter. The rate of feed of the sterol containing source material to the wiped film evaporator is approximately 1 kilogram per minute. In established operation the temperature at the top of the wall of the wiped film evaporator is about 185° C. and the temperature of the wall at the bottom of the wiped film evaporator is about 270° C. The temperature incrementally increases down the wall of the wiped film evaporator as the sterol containing source material becomes hotter.

The vapor temperature of the components flashed off the wall of the wiped film evaporator is determined at a point obtained by proceeding one-half the distance on a radial from the outer surface of the conduit to the inner surface of the wall at the midpoint thereof. Coolant is passed through the conduit at a temperature of not less than 95° C. This temperature is for convenience in avoiding build-up of the condensed sterol distillate on the outer surface of the conduit. It is of course possible to use lower temperatures, but then the conduit must be periodically cleaned. As previously described, the distillate obtained from the sterol containing source material condenses on the conduit and flows down the conduit and into the sump where it is removed for further processing.

In operation the blades of the wiped film evaporator are set to keep the thickness of the film on the wall at about 2 to 3 millimeters. The residence time of the sterol containing source material on the wall of the wiped film evaporator is about 15 seconds for a flash distillation. Longer periods of time may be allowed up to about 15 minutes but then lower temperature ranges and higher vacuums are required and as well the rate of feed of the sterol containing source material and the purity of the distillate are lessened slightly.

The vacuum held on the wiped film evaporator in the present example is 1 millimeter of mercury at absolute pressure. The distillate including the sterols and the organic impurities collected at the sump represent about 90% by weight of the sterol containing source material fed into the wiped film evaporator. The sterol content of the distillate is 15% greater than that of the sterol containing source material. The residue containing the ferric chloride, higher boiling components and some degraded sterol are collected in the reservoir and discarded. The ratio of the sitosterol, campesterol, and stigmasterol in the distillate is essentially the same as that in the sterol containing source material. The present invention is so effective that no ferric chloride is found in the distillate as determined by ash content.

The foregoing process may also be carried out by conventional glassware distillation, however, greater care must be taken to avoid degradation of the sterols during the distillation. As was previously noted, the present invention not only applies to obtaining mixtures of sterols free from Friedel-Crafts catalyst but also to the purification of a single sterol which has been contaminated with such a catalyst.

What is claimed is:

1. The process of purifying sterols from a sterol containing source material having present therein sterols and ferric chloride wherein the sterol containing source material is first degassed and then subjected to flash distillation to yield as a distillate the sterols wherein the sterols are in about the same relative proportion to one another as in the sterol containing source material, and a residue containing the ferric chloride.

2. The process of claim 1 wherein the vapor temperature of the distillate upon distillation is from about 160° C. to about 265° C.

3. The process of claim 1 wherein a given portion of the source material is rendered substantially free of the ferric chloride in a period of less than about one minute.

4. The process of claim 1 wherein the source material is subjected to a vacuum of from about 0.1 mm to about 4 mm Hg in the distillation process.

5. The process of claim 1 wherein the source material is distilled such that less than 15% by weight of the source material reaches a temperature in excess of 300° C. during the distillation.

6. The process of claim 1 wherein a given portion of the source material is rendered substantially free of the ferric chloride in a period of less than about 1 minute.

7. The process of claim 1 wherein the temperature of the source material immediately prior to the distillation is from about 135° C. to about 200° C.

8. The process of claim 1 wherein the sterol containing source material is derived from soy sludge.

9. The process of claim 1 wherein the sterol containing source material includes sterols selected from the group consisting of sitosterol, stigmasterol, and campesterol and mixtures thereof.

* * * * *